United States Patent [19]

Suzuki et al.

[11] Patent Number: 4,687,477

[45] Date of Patent: Aug. 18, 1987

[54] DISPOSABLE DIAPER AND METHOD FOR INCORPORATION OF ELASTIC MEMBER INTO SUCH DIAPER

[75] Inventors: Migaku Suzuki; Satoshi Sasaki; Takashi Mitsuno; Hiroyuki Inagaki, all of Ehime, Japan

[73] Assignee: Uni-Charm Corporation, Ehime, Japan

[21] Appl. No.: 899,421

[22] Filed: Aug. 22, 1986

Related U.S. Application Data

[60] Division of Ser. No. 755,369, Jul. 16, 1985, Pat. No. 4,626,305, which is a continuation of Ser. No. 460,909, Jan. 25, 1983, abandoned.

[30] Foreign Application Priority Data

Apr. 14, 1982 [JP] Japan ................................. 57-61946

[51] Int. Cl.⁴ ............................................. A61F 13/16
[52] U.S. Cl. ................................................ 604/385 A
[58] Field of Search .................. 604/385.2, 385.1, 358, 604/366, 370

[56] References Cited

U.S. PATENT DOCUMENTS

| | | | |
|---|---|---|---|
| 4,300,562 | 11/1981 | Pieniak | 604/385.2 |
| 4,397,645 | 8/1983 | Buell | 604/385.1 |
| 4,407,284 | 10/1983 | Pieniak | 604/385.2 |
| 4,555,244 | 11/1985 | Buell | 604/385.2 |
| 4,601,717 | 7/1986 | Blevins | 604/385.1 |

Primary Examiner—John D. Yasko
Attorney, Agent, or Firm—Fred Philpitt

[57] ABSTRACT

A disposable diaper provided with elastic members respectively comprising a plurality of rubber strings in respective side flaps of the diaper so that these elastic members provide a plurality of longitudinally extending elastic lines in said side flaps to provide a good fit of said side flaps around infant's thighs.

4 Claims, 12 Drawing Figures

DISPOSABLE DIAPER AND METHOD FOR INCORPORATION OF ELASTIC MEMBER INTO SUCH DIAPER

This is a division of application Ser. No. 755,369 filed July 16, 1985, now U.S. Pat. No. 4,626,305, which is a continuation of Ser. No. 460,909 filed Jan. 25, 1983, now abandoned, and the benefits of 35 USC 120 are claimed relative to it.

BACKGROUND OF THE INVENTION

The present invention relates to disposable diaper and a method for incorporation of elastic members into such diaper. More particularly, the present invention relates to a construction of elastic members functioning to fit both side flaps of the disposable diaper of underpant type around infant's thighs and a method to incorporate such elastic members into said diaper.

The elastic members functioning to fit both side flaps of the disposable diaper around infant's thighs has already been adopted by the well known disposable diapers of underpant type and the most typical one of such diapers of prior art has been disclosed by U.S. Pat. No. 3,860,003. Usually, a single rubber tape has been incorporated into each side flap of the diaper as the elastic member. However, the diaper incorporated with such elastic members of single rubber tape type exerts a localized or linear high pressure around infant's thighs with linear pressure marks remaining around infant's thighs and sometimes causes a pain for the infant who wears such diaper particularly when the infant wears this for a relatively long period.

To eliminate such drawback, it has already been proposed to use the rubber tape which is formed relatively wide, as said elastic member. However, use of the rubber tape formed in such manner would be disadvantageous in the following aspect.

In view of the molding technique, it is difficult to obtain a rubber tape substantially thinner than the rubber tape which has usually been used as said elastic member and it would be almost impossible to obtain the rubber tape of uniform thickness even if molding of extremely thin rubber tape is possible. Accordingly, if the conventional rubber tape used as the elastic member is formed wider and incorporated into the diaper at the stretching ratio similar to that as used with the conventional rubber tape, a pressure around infant's thighs would be excessive, since the tensile stress thereof is too high. To obtain an elastic member having a tensile stress which is regarded optimal for a pressure to be exerted around infant's thigh, therefore, it is necessary to reduce the stretching ratio of said elastic member by a quantity corresponding to an increased width of said elastic member. This would result in an increase of cost due to an additional quantity of material for the elastic member required to enlarge the width thereof as well as due to an additional quantity of material for said elastic member required to reduce the stretching ratio thereof. Such increased cost is seriously disadvantageous for the disposable diaper which should be manufactured at a reasonably low cost.

It is certainly possible to overcome this drawback when several fine rubber strings are used as the elastic member, as will be understood from reading a further later description on the present invention. However, such a measure confronts a difficulty, namely, the disposable diaper must be mass-produced at a low cost and the rubber strings must be secured, by means of adhesive, to a backsheet comprising plastic film or the like and/or to a topsheet comprising nonwoven fabric or the like, both sheets being constituent members of the diaper. Furthermore, said drawback can be effectively overcome only when said rubber strings used as the elastic member are substantially finer than the rubber tape conventionally used as said elastic member of the diaper. However, finer the rubber strings to be used as the elastic member are and more the number of these rubber strings is, more difficult the handling of these rubber strings for securing them to said sheet(s) by means of adhesive and the operational efficiency is inevitably reduced.

An object of the present invention is, therefore, to provide an improved disposable diaper provided with elastic members respective comprising several rubber strings substantially finer the rubber tapes conventionally used as the elastic members of the disposable diaper and arranged at appropriate intervals in parallel within side flaps of the diaper so as to form several elastically stretchable lines in the respective side flaps and thereby to make good fit of said side flaps around infant's thighs.

Another object of the present invention is to provide an improved disposable diaper in which a plurality of extremely fine rubber strings arranged at appropriate intervals in parallel are used as the elastic members as previously mentioned so that the stretching ratio of these rubber strings may be increased while the length of these rubber strings to be used may be reduced with respect to the conventional rubber tapes commonly used as the elastic members in the disposable diapers of prior art and, as a result, the quantity of rubber material used for these elastic members may be sufficiently reduced to achieve production of the diaper at a low cost.

Still another object of the present invention is to provide an improved method for incorporation of said plurality of rubber strings serving as the elastic members into associated components of the disposable diaper comprising steps of continuously feeding these rubber strings, particularly, those in the form of respective single rubber tapes held by apparent side-by-side joints each having an intrinsic separability to said associated components while separating them into a predetermined number of rubber strings in neat order, and then securing these rubber strings to said components by adhesive so that the desired incorporation of these rubber strings into the diaper may be achieved at a high efficiency.

The other objects of the present invention will be apparent from the following description of the invention.

SUMMARY OF THE INVENTION

According to the present invention, there is provided an improvement in the disposable diaper including a topsheet, a backsheet, an absorbent body fixedly interposed between said both sheets and elastic members arranged in respective side flaps formed by portions of said both sheets extending beyond opposite outer edges of said absorbent body so as to be closely laid upon one another so that longitudinal elastic lines are formed in said side flaps to fit said side flaps around infant's thighs, said elastic members respectively comprising three (3) to forty-five (45) rubber strings each having a cross-sectional area of 0.03 mm$^2$ to 0.45 mm$^2$ and totally having a cross-sectional area of 0.09 mm$^2$ to 1.35 mm$^2$, being stretched at a stretching ratio of 100% to 400% and simultaneously secured by adhesive within the respective side flaps at appropriate intervals in parallel so that three (3) to forty-five (45) elastic lines may be formed in said respective side flaps for good fit of these side flaps around infant's thighs. There is provided also, in accordance with the present invention, an improved method for incorporation of these elastic members into said diaper.

BRIEF DESCRIPTION OF THE DRAWING

FIG. 3(A) and (B) is a partial perspective view generally showing the elastic members of particular cross sections which can be used within a scope of the present invention;

PREFERRED EMBODIMENTS OF THE INVENTION

Preferred embodiments of the present invention will be described in reference with the accompanying drawing.

Figure 1:
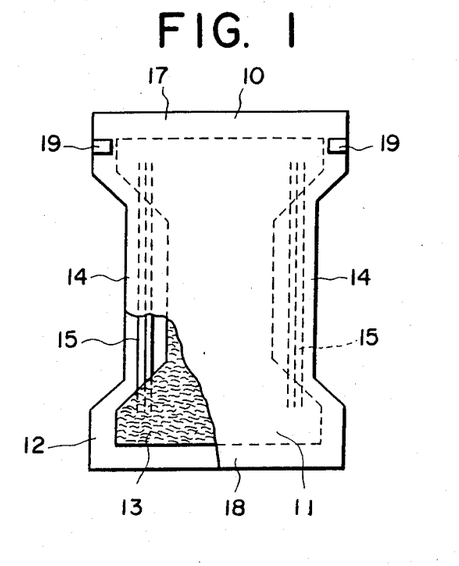
FIG. 1 is a developed plan view showing, partially broken away, an embodiment of the disposable diaper constructed according to the present invention.
Figure 2:
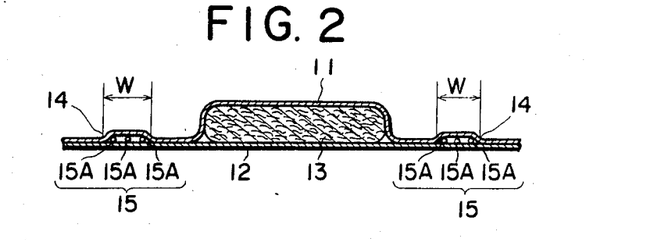
FIG. 2 is a sectional view taken along the centre line of the diaper as shown by FIG. 1.

Referring to FIGS. 1 and 2, a disposable diaper 10 includes a water permeable topsheet 11 of nonwoven fabric or the like, a water impermeable backsheet 12 of plastic film or the like, an absorbent body 13 of fluffed wood pulp or the like, and elastic members 15 arranged within respective side flaps 14 formed by portions of the both sheets 11, 12 extending beyond opposite outer edges of the absorbent body 13 so as to be closely laid upon one another so that said elastic members 15 be elastically stretchable in the longitudinal direction. Such diaper 10 is, when attaching this to an infant, assembled by adhesively connecting pressure-sensitive fastening tapes which have previously been attached to opposite ends of one waist portion 17 to corresponding opposite ends of the other waist portion 18. The elastic members 15 respectively comprise a plurality of rubber strings according to the present invention, as will be described later more in detail, and the disposable diaper having the above-mentioned construction in which each elastic member comprises a single rubber tape is well known from, for example, said U.S. Pat. No. 3,860,003.

Figure 3:
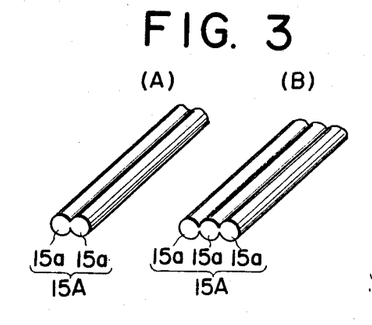

Although FIGS. 1 and 2 show the diaper 10 having the elastic members 15 respectively comprising parallelly spaced three rubber strings 15A in the respective side flaps 14, it is also possible within the scope of the present invention to use the elastic members 15 respectively comprising three (3) to forty-five (45) rubber strings each having a cross-sectional area of 0.03 mm$^2$ to 0.45 mm$^2$ and totally having a cross-sectional area of 0.09 mm$^2$ to 1.35 mm$^2$ parallelly spaced one from another in the respective side flaps 14. These rubber strings 15A may be of uniform cross-sectional area or, in some cases, certain strings among them may be of different cross-sectional area. In the latter case, it will be reasonable that the rubber strings 15A of relatively small cross-sectional area are arranged on the inner side within the respective side flaps 14 and the rubber strings 15A of relatively large cross-sectional area are arranged on the outer side within the respective side flaps 14. However, the elastic members 15 of the former type are preferably used for execution of the method according to the present invention which will be described later. In the diaper 10 according to the present invention using such elastic members 15 respectively comprising three (3) to forty-five (45) rubber strings 15A in the respective side flaps 14, there are provided in the respective side flaps 14 three (3) to forty-five (45) elastically stretchable lines which function to fit the side flaps around infant's thighs. The respective rubber strings 15A may have circular, elliptical or square cross-sections. Further, a plurality of rubber string elements 15a may be integrally joined side-by-side in parallel so as to form each rubber string 15A having a combined cross-section as shown by FIG. 3(A) or 3(B). The rubber strings 15A each having such combined cross-section corresponding to a plurality of circles joined to one another may be obtained by, for example, molding the respective rubber string elements 15a and then by fusing them together before they are sufficiently cooled to be solidified.

When a plurality of rubber strings 15A are used as each of the elastic members 15, the tensile stress is reduced and the stretching ratio is increased in comparsion to a single rubber tape used as the elastic member even when the total cross-sectional area, the material and the stretching ratio of said rubber strings 15A are identical to those of said single rubber tape. And also the tolerable range of uneven stretching ratio is enlarged when said plurality of rubber strings 15A are used as the elastic member 15. This will be readily understood from FIGS. 11 and 12 showing result of the experiment conducted by the inventors.

Figure 11:
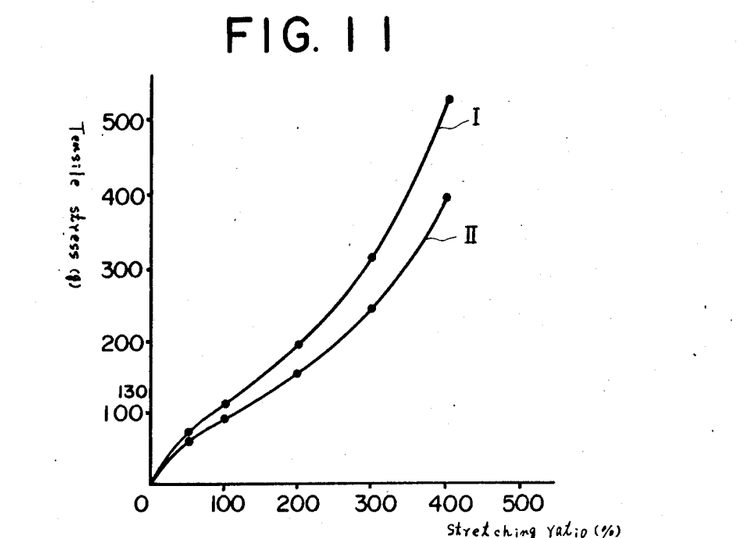
FIGS. 11 and 12 are diagrams showing characteristic curves exhibited when a single rubber tape is used and when a group of several rubber strings is used as each of the elastic members, respectively.

FIG. 11 is a diagram showing characteristic curves exhibited by samples I, II for comparison when these samples are subjected to a tensile stress (g) varying as given on the ordinate with a stretching ratio (%) varying as given on the abscissa. The sample I comprises a single rubber tape of natural rubber which is 100 mm long, 6.6 mm wide and 0.2 mm thick while the sample II comprises three separate rubber tapes each of which is equally 3.2 mm wide. To generate a tensile stress of 130 g in each elastic member which has been found to provide the optimal pressure around infant's thigh, for example, the sample I can be stretched as slightly as by approximately 120% while the sample II can be tolerably stretched as extensively as by approximately 170%.

Figure 12:
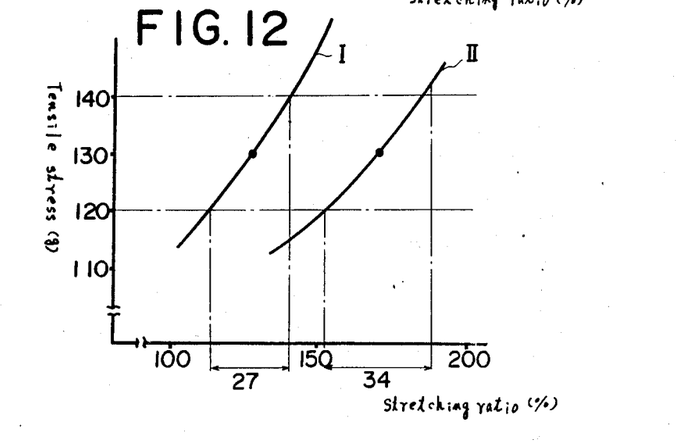

FIG. 12 is a schematic diagram corresponding to the partially enlarged FIG. 11, showing the tolerable range of uneven stretching ratios for the respective samples I, II when these samples I, II were incorporated into the associated diapers with the tensile stress of 130 g±10 g as requirement for the diaper design. Concerning the tolerable range of uneven stretching ratio, the experimental result indicated approximately 27% for the sample I and 34% for the sample II. The tolerable range of uneven stretching ratio for the sample II is thus larger than that for the sample I, so that such construction of the sample II facilitates a draft adjustment of the elastic member on a step of its drafting treatment during execution of the method according to the present invention.

As seen from such result of the experiment conducted by the inventors, use of a plurality of rubber strings 15A as the elastic member 15 corresponding to a single rubber tape divided into several rubber tapes allows a stretching ratio higher than the case in which said single rubber type is used as said elastic member to be adopted so as to obtain a desired pressure around infant's thigh, since the tensile stress is lower in the former case than in the latter case. In other words, the length of the elastic member 15 may be economically reduced. In consequence, the diaper according to the present invention in which a plurality of rubber strings 15A are used as the elastic member 15, a quantity of material to be used for the elastic member 15 is reduced in comparison with the diaper of prior art in which a single rubber tape is usually used as each of the elastic members 15 and each diaper can be manufactured at the correspondingly reduced cost.

The rubber strings 15A serving as the elastic member have their tensile stress lowered as the number thereof increases, so that a correspondingly higher stretching ratio may be used to increase said advantage. However, study by the inventors has shown that, with each elastic member comprising three (3) to forty-five (45) natural rubber strings of 0.03 mm$^2$ to 0.45 mm$^2$ in individual cross-sectional area and of 0.09 mm$^2$ to 1.35 mm$^2$ in total cross-sectional area, the tensile stress thereof sharply increases when the stretching ratio thereof excesses 400%, and as a result, a pressure mark clearly remains around infant's thigh. Accordingly, for the diaper according to the present invention, the respective elastic members 15 are subjected to a drafting effect when these elastic members are incorporated into the diaper so that a stretching ratio of 100% to 400%, preferably of 150% to 350%, more preferably of 250% to 300%, may be attained. At a stretching ratio lower than 100%, a quantity of rubber material to be used should be uneconomically increased. It should be noted here that a single rubber tape, for example, 0.20 mm thick and 6.6 mm wide has usually been used as such elastic member, wherein said single rubber tape has usually been subjected to a drafting effect at a stretching ratio of 70% to 100% when this single rubber tape is incorporated into each side flap of the diaper. The expression "stretching ratio of 100%" is used here to indicate the case in which the elastic member having its initial length of 100 mm was stretched until a length of 200 mm is attained.

Into the disposable diaper constructed according to the present invention a plurality of rubber strings 15A each of a relatively small cross-sectional area are incorporated as the elastic member 15 in parallel at side-by-side spacings, so that the apparent width of the respective elastic members in the associated side flaps (as indicated by W in FIG. 2) is enlarged with respect to the case in which a single rubber tape is used as the elastic member as in the diaper of prior art and a pressure around infant's thigh is correspondingly reduced. In consequence, a pain for the infants often suffer from wearing the diaper of prior art as well as a pressure mark appearing on infant's thigh as a result of wearing such diaper of prior art are substantially eliminated by the diaper constructed in accordance with the present invention. To achieve such effect, although it depends more or less upon characteristics such as rigidity of the topsheet 11, the backsheet 12 and the absorbent body 13 which are components of the diaper, a plurality of rubber strings 15A used as the respective elastic members 15 are arranged within ranges preferably 10 mm to 35 mm and more preferably 15 mm to 20 mm wide outwardly from the respective outer edges of the absorbent body.

During use of the diaper constructed according to the present invention, the elastic members 15 respectively comprising a plurality of rubber strings 15A function as if these elastic members 15 are respectively integrated pieces but they are really separated into the individual rubber strings 15A, respectively, so that these rubber strings 15A are independently stretched and contracted to facilitate the desired fit around infant's thighs. The fact that the elastic members 15 are really separated into a plurality of rubber strings 15A is advantageous to maintain a proper air-permeability in the regions of these elastic members 15.

Figure 4:
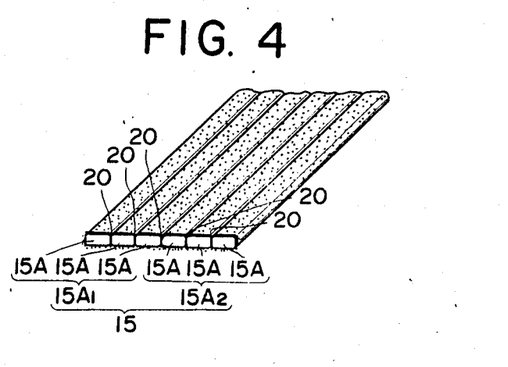
FIG. 4 is a partial perspective view showing an embodiment of the elastic member which can be used for execution of the method according to the present invention.

FIG. 4 shows an embodiment of the elastic member 15 to be used for execution of the method according to the present invention. The elastic member 15 comprises six rubber strings 15A substantially same in their square cross-sections and these rubber strings 15A are maintained in the form of a single tape by provisional side-by-side joints but have intrinsic separability from one another. Such joints 20 of the individual rubber strings 15A are lines of fable bonding by fusion or provisional joints which may be provided by spraying powder such as talc onto the individual rubber strings 15A immediately after these rubber strings have been molded to prevent these rubber strings from sticking to the other objects and bringing these rubber strings into light contact with one another. Said powder clinging to the respective rubber strings 15A may be removed, if necessary, in actual use of these rubber strings 15A. Further, said provisional joints 20 may be easily torn off by a slight force laterally exerted thereon and said rubber strings 15A may be neatly separated along said provisional joints 20. Such provisionally joined assembly of six (6) to ninety (90) individual rubber strings 15A may be used as the elastic members 15, since three (3) to forty-five (45) rubber strings 15A are incorporated into each side flap 14 of the diaper 10 according to the present invention as previously described. The assembly of thus provisionally joined rubber strings is manufactured by Rondex Co., Ltd. (Kohoku-Ku, Yokohama, Japan) and commercially available under the trade name "RONDEX".

Figure 5:
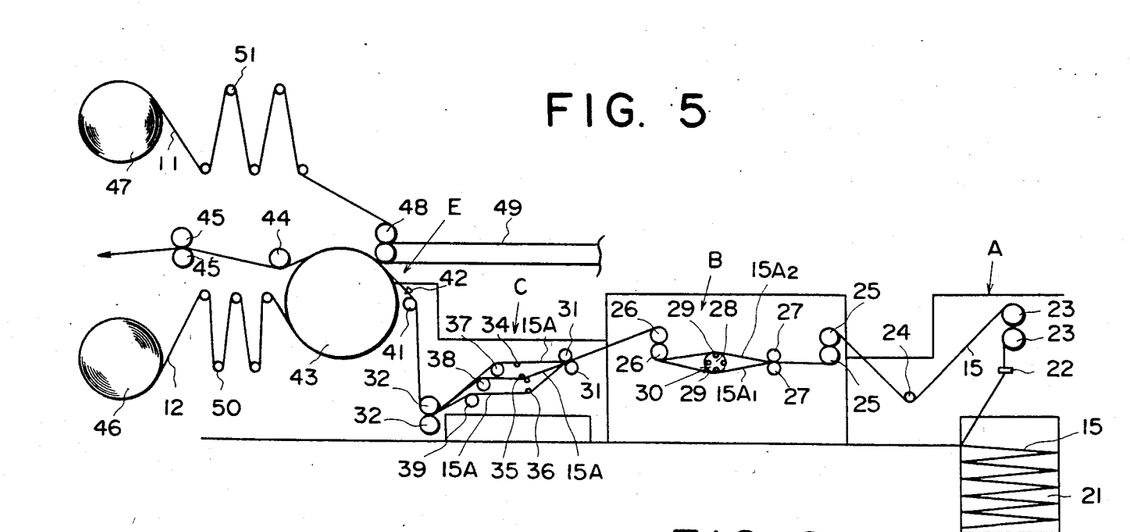
FIG. 5 is a schematic side view partially showing an apparatus for production of the disposable diaper according to the present invention.
Figure 6:
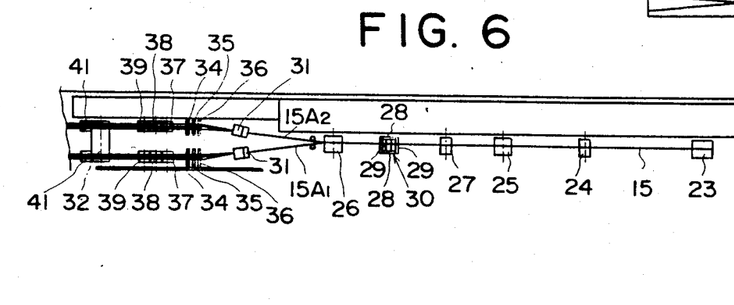
FIG. 6 is a plan view showing a dividing station for the elastic member in the apparatus as shown by FIG. 5.
Figures 7, 8:
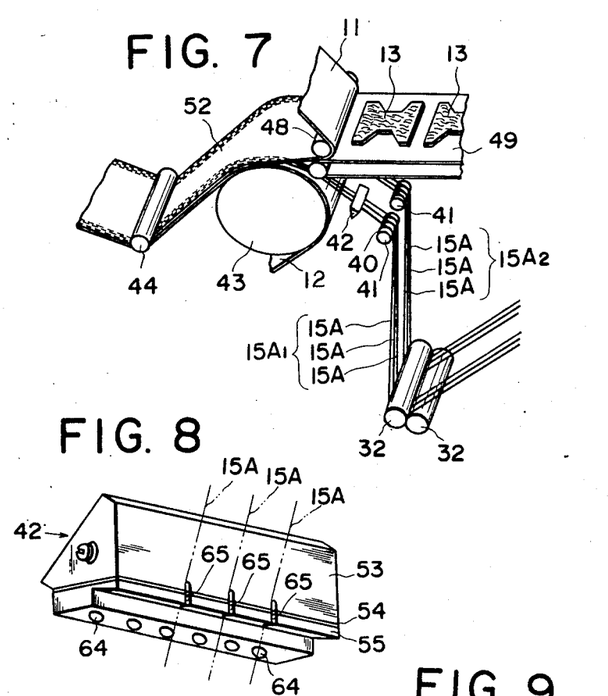
FIG. 7 is a schematic perspective view showing a mechanical station for adhesive fixation of the elastic members to the diaper.
FIG. 8 is a perspective view showing a nozzle serving for application or adhesive to the elastic members.

FIGS. 5 through 7 schematically illustrate an apparatus for execution of the method according to the present invention. This apparatus comprises a feeding station A, a drafting station B, a separating station C and an applying station E, respectively, of the elastic members 15.

The feeding station A includes a storage container 21, a guide ring 22 and a pair of guide rolls 23, 24, respectively, of the elastic members 15 to be introduced from said feeding station A to the drafting station B.

The drafting station B includes a pair of squeezing rolls 25, 25, another pair of squeezing rolls 26, 26 of a circumferential velocity higher than that of said pair of squeezing rolls 25, 25, a pair of cleaning rolls 27, 27 and a beating roll 30, these last-mentioned two components being arranged between said first pair of squeezing rolls 25, 25 and said second pair of squeezing rolls 26, 26, and said beating roll 30 being provided with several rods 29 extending between opposite end plates 28 to which the respective ends of said rods 29 are fixed along the circumferences of the respective end plates 28 at circumferentially equal intervals. Each elastic member 15 is subjected to a drafting effect at a desired stretching ratio between said two pairs of squeezing rolls 25, 25 and 26, 26 while the previously mentioned powder clinging to the elastic member 15 is removed by the pair of cleaning rolls 27, and then the elastic member 15 is beaten by the beating roll 30. A quantity of powder thus removed by the cleaning rolls from the elastic member 15 is recovered by suction means or the like arranged adjacent said pair of cleaning rolls 27 into a reservoir (not shown). Although the elastic member 15 which can be treated by the apparatus as shown by FIGS. 5 through 7 is not limited to that of the art as shown by FIG. 4, description will be made with respect to the embodiment of the elastic member 15 as shown by FIG. 4, for convenience of explanation. The elastic member 15 comprising six (6) rubber strings 15A provisionally joined in parallel as previously mentioned is now divided into two blocks, i.e , an upper block $15A_2$ and a lower block $15A_1$ which are respectively guided along upper and lower sides of the beating roll 30 interposed between these two blocks $15A_1$, $15A_2$. The elastic member 15 is drafted by the second pair of squeezing rolls 26, 26 as said elastic member 15 is guided along said beating roll 30 and thereby successively divided into the respective blocks $15A_1$, $15A_2$. Simultaneously, the beating roll 30 functions to beat these blocks $15A_1$, $15A_2$ so that these blocks may be easily separated in the separating station C further into the individual rubber strings 15A, and then introduced into said separating station C.

The separating station C includes pairs of squeezing rolls 31, 31, other pairs of squeezing rolls 32, 32, guide rods 34, 35, 36 arranged at different levels and guide rolls 37, 38, 39, associated with said guide rods 34, 35, 36, respectively, between said pairs of squeezing rolls 31, 31 and said pairs of squeezing rolls 32, 32. The respective blocks $15A_1$, $15A_2$ are separated into the individual rubber strings 15A. The first rubber string 15A of each block is put against the guide rod 34 and then the upper side of the guide roll 37, the second rubber string 15A is put against the guide rod 35 and then the upper side of the guide roll 38, and the third rubber string 15A is put against the guide rod 36 and then the upper side of the guide roll 39. The respective blocks $15A_1$, $15A_2$ thus suspended on the associated guide rods and guide rolls are guided between the pairs of squeezing rolls 32, 32 while these blocks are maintained in said stretched state and thereby the respective blocks $15A_1$, $15A_2$ are successively separated into the individual rubber strings 15A as already mentioned under the tearing effect by said guide rods 34, 35, 36 and said guide rolls 37, 38, 39. Thus these individual rubber strings 15A are introduced into the applying station E.

The applying station E includes guide rolls 41 provided on the peripheral surfaces with a plurality of grooves 40 (FIG. 7), nozzle means 42 and a chilling roll 43. There are provided in the vicinity of the applying station E a pressure roll 44, a pair of squeezing rolls 45, 45, a supply roll 46 serving to support plastic film 12 for the backsheet of diaper wound therearound, a supply roll 47 serving to support nonwoven fabric 11 for the topsheet of diaper wound therearound, a guide roll 48, a conveyor 49 serving to convey the absorbent body 13 of diaper, guide rolls 50, 51 and the others. The individual rubber strings 15A are guided by the associated guide rolls 41 along the grooves 40 formed therearound and pass by the associated nozzle means 42 by which said individual rubber strings 15A are applied with adhesive of hot melt type and simultaneously regulated with respect to the intervals at which said individual rubber strings 15A are to be arranged on the associated side flaps of diaper. The individual rubber strings 15A are continuously sticked, while maintained in said stretched state, to the upper surface of the plastic film 12 along opposite side zones thereof, said plastic film 12 being continuously introduced onto the upper side of the chilling roll 43, and the latter functions also to chill said adhesive and thereby to solidify it. As seen from FIG. 7, the nonwoven fabric 11 is introduced by the guide roll 48 onto the upper side of said plastic film 12 while the respective absorbent bodies 13 which have previously been formed are conveyed by the conveyor 49 longitudinally at regular intervals into a gap between said nonwoven fabric 11 and said plastic film 12 so as to be held therebetween. The nonwoven fabric 11 and the plastic film 12 are applied by separate nozzle means (not shown) arranged at desired positions with adhesive of hot melt type on their inner sides before these nonwoven fabric 11 and plastic film 12 are laid upon one another, and then joined so that said absorbent bodies 13 are secured at regular intervals as above mentioned. Continuous pieces of diaper 52 is now pressed by the pressure roll 44 and transferred to the subsequent process (not shown) in which said continuous diaper 52 will be cut into individual diaper 10 as shown by FIG. 1.

Figures 9, 10:
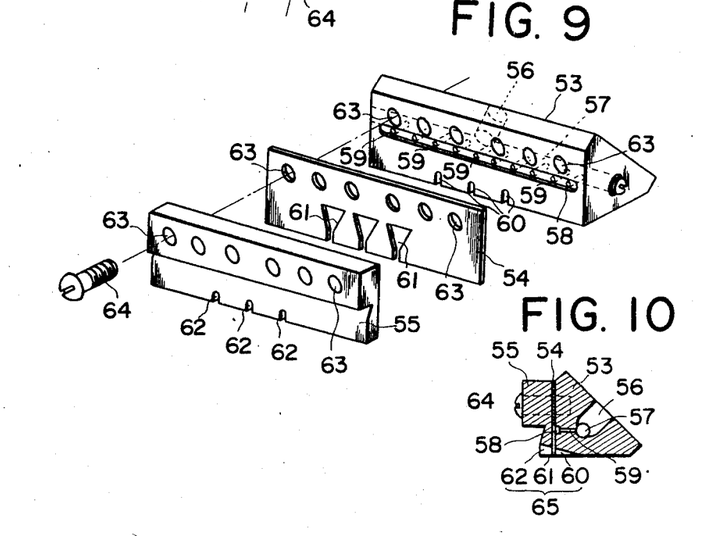
FIG. 9 is a developed perspective view of said nozzle as shown by FIG. 8.
FIG. 10 is a sectional view taken along the centre line of the nozzle as shown by FIG. 8.

FIGS. 8 through 10 illustrate an embodiment of said nozzle means 42. The nozzle means 42 comprises a triangular prism-like first member 53, a plate-like second member 54 and a plate-like third member 55. The first member 53 includes an inlet hole 56 opening at the centre of one side wall, distribution channel 57 communicating with said inlet hole 56 and extending longitudinally of said first member 53, a plurality of jet orifices 59 communicating with said distribution channel 57 and opening, at regular intervals, into an elongate recess 58 formed longitudinally in another side wall, and a plurality of slits 60 formed at regular intervals in one end of said first member 53. The second member 54 includes a plurality of triangular slits 61 at the same intervals as said slits 60 in one end of said second member 54. The third member 55 also includes a plurality of slits 62 at the same intervals as said slits 60 in one end of said third member 55. The first member 53, the second member 54 and the third member 55 are united into complete nozzle means 42 when screws 64 are threaded into corresponding threaded holes formed in these three members. The nozzle means 42 of such construction is arranged in a path of three rubber strings 15A as each elastic member 15 between said guide roll 41 and said chilling roll 43 as seen in FIG. 5 so that slots 65 respectively comprising said slits 60, 61, 62 are directed downwards. A reservoir (not shown) adapted to control or regulate supply, blocking and metering of adhesive of hot melt type is connected with the inlet hole 56. When passing through the respective slots 65, the respective three rubber strings 15A as each elastic member 15 are applied with said adhesive of hot melt type supplied from said reservoir through said inlet hole 56, said distribution channel 57, said jet orifices 59 and said elongate recess 58 to the respective slots 65 and sprayed these slots 65. An excessive quantity of said adhesive of hot melt type which has not been applied on the elastic member 15 is recovered into a reservoir (not shown) placed under the nozzle means 42.

It is preferred that the elastic member 15 is applied with a proper quantity of said adhesive of hot melt type at a proper temperature. The experiment conducted by the inventors indicated that the already mentioned natural rubber strings 15A each having a cross-sectional area of approximately 0.185 mm$^2$ supplied from said Rondex Co., Ltd. under the trade name "RONDEX 3SR" is one of preferred products to be used as the elastic member 15. When this particular product is used as material for the elastic member 15, a preferable quantity of said adhesive of hot melt type to be applied on one of such rubber strings 15A is 0.1 to 0.2 g/m and a preferred temperature for application is a temperature lower than 165° C. A quantity of application smaller than 0.1 g/m, in this case, would prevent the elastic members 15 from being reliably sticked to the side flaps 14 of the diaper 10 while a quantity more than 0.2 g/m would cause exudation of said adhesive through the topsheet 12 of the diaper 10, discomfort for the wearer after solidified, and increase of the manufacturing cost. Said temperature for application being 165° C. or higher would result in deterioration or even breakage of the rubber strings 15A. It has been found also that, as said adhesive of hot melt type, such adhesive which is commercially available in our country under the trade name "KANEBO NSC MQ-975" and presents its viscosity of 120,000 cps and 220,000 cps at the temperature of 120° C. and 150° C., respectively is one of preferred products.

The number of the slots 65 depends on the number of the rubber strings 15A to be parallelly arranged in the respective side flaps 14 of the diaper 10. The intervals at which the respective slots 65 are arranged function to regulate the intervals at which the rubber strings 15A are parallelly arranged in the respective side flaps 14 of the diaper 10.

Although the method according to the present invention has been described hereinbefore in reference with FIGS. 5 through 7 showing the apparatus for execution of the inventive method, in which each elastic member 15 comprising a desired number of rubber strings 15A joined in parallel one another is divided into two blocks 15A$_1$, 15A$_2$ while these rubber strings 15A are stretched and then these two blocks 15A$_1$, 15A$_2$ are further separated into the individual rubber strings 15A, respectively, the other manners as following are also covered by the scope of the method according to the present invention:

(a) the elastic member 15 comprising a desired number of rubber strings 15A parallelly joined one to another are separated into the individual rubber strings 15A while said elastic member 15 is placed under a drafting effect;

(b) the elastic member 15 comprising a desired number of rubber strings 15A parallelly joined one to another is divided into two blocks 15A$_1$, 15A$_2$ after stretched, and then these two blocks 15A$_1$, 15A$_2$ are further separated into the individual rubber strings 15A; and (c) the elastic member 15 comprising a desired number of rubber strings 15A parallelly joined one to another is separated into the individual rubber strings 15A after stretched.

Apparatuses adapted for execution of these manners (a) through (c) are not shown but may be readily designed by those skilled in the art in reference with the apparatus as shown by FIGS. 5 through 7.

The elastic member 15 comprising a plurality of rubber strings 15 provisionally joined in parallel one to another is used according to the inventive method, as already mentioned, so that said individual rubber strings 15A are free from entanglement or breakage during treatments in said supplying station A and drafting station B. Further, the rubber strings 15A have their intervals regulated by the respective slots 65 of the nozzle means 42 and are applied therearound with adhesive so that each elastic member 15 may be reliably secured in each side flap 14 of the diaper 10. Accordingly, the method according to the present invention enables the elastic members 15 to be efficiently incorporated into the diaper 10 even though these elastic members 15 respectively comprise a plurality of extremely fine rubber strings 15A.

EXAMPLE

The absorbent body made of fluffy wood pulp having a unit weight of 450 g/m$^2$ was interposed between the topsheet, 330 mm×450 mm, 35 g/m$^2$ consisting of 50 weight % polyester fibre and 50 weight % rayon fibre, and the backsheet, 330 mm×450 mm consisting of 25 $\mu$ thick polyethylene film; these topsheet, backsheet and absorbent body were fixedly assembled together by means of adhesive agent of hot melt type; and the elastic members were adhesively incorporated into both side flaps formed by the portions of said both sheets which extend outwardly beyond the respective outer edges of said absorbent body and are laid upon one another, so as to obtain a complete diaper as shown by FIG. 1. The elastic members respectively consisted of three natural rubber strings (total cross-sectional area: 1.32 mm$^2$) each of which was 160 mm long, 0.2 mm thick and 2.2 mm wide. These three rubber strings were arranged in parallel at the intervals of 9 mm while they were stretched to a length of 450 mm so that a tensile stress of 130 g is reached. These elastic members were applied with adhesive agent of hot melt type at the temperature of 160° C., in a quantity of 0.2 g/m for each string. The adhesive agent used herein had a viscosity of 20000 cps/160° C. and a softening point of 97° C.

As a control product, a diaper in which the number of rubber strings is different from the above mentioned example was made. In this control diaper, the elastic members respectively comprising a single rubber tape which is 195 mm long, 0.2 mm thick and 6.6 mm wide (cross-sectional area: 1.32 mm$^2$) were adhesively secured into the respective side flaps while said elastic members were stretched so that a length of 450 mm may be obtained with a tensile stress of approximately 130 g.

Said product according to the present invention and said control product were attached to 100 infants each weighing 5500 to 11000 g and tested with respect to urine leakage and pressure mark, and the following result was obtained.

|  | Leakage test | | Pressure mark test | | |
| --- | --- | --- | --- | --- | --- |
|  | No leakage | Slight leakage | Clear mark | Slight mark | No mark |
| Inventive product | 88 | 12 | 16 | 43 | 41 |
| Control product | 83 | 17 | 42 | 37 | 21 |

Concerning the quantity of material used for the elastic member, the initial dimension of 160 mm was necessary for the inventive product to obtain the desired tensile stress while the initial dimension of 195 mm for the control product to obtain the same tensile stress. It is obvious from this result that the product according to the present invention is economically advantageous compared to the control product.

What is claimed is:

1. A disposable diaper including
   (A) a water permeable topsheet,
   (B) a water impermeable backsheet overlying said topsheet,
   (C) an absorbent body fixedly interposed between said sheets and inwardly of the perimeter of said sheets so as to leave side flaps extending beyond the opposite outer edges of the absorbent body, and
   (D) elastic means disposed between said sheets in each of said side flaps, each of said elastic means
      (1) comprising a group of 3–45 elastic strings disposed in close parallel relationship to each other and in such a manner that the elastic strings are intrinsically separate from one another,
      (2) being stretched at a stretching ratio of 100–400%,
      said elastic strings
      (a) each being longitudinally extendable,
      (b) each having a cross-sectional area of 0.03-0.45 mm$^2$,
      (c) having a total cross-sectional area of 0.09-1.35 mm$^2$,
   whereby the longitudinal lines of elasticity formed in said side flaps permit said slide flaps to effect a good fit around an infant's thighs.

2. A diaper according to claim 1 wherein said plurality of elastic strings span a width of between 10 and 35 mm.

3. A diaper according to claim 1 wherein the ends of said elastic strings are anchored between said sheets in the same area where a portion of said absorbent body is fixed.

4. A diaper according to claim 1 wherein said elastic strings in a group are of different cross-sectional area, the strings of smaller cross-sectional area being arranged toward the inner side of said side flaps and the strings of larger cross-sectional area being arranged toward the outer side of said side flaps.

* * * * *